(12) United States Patent
Lee et al.

(10) Patent No.: US 11,007,524 B2
(45) Date of Patent: May 18, 2021

(54) AUTOMATIC MICROFLUIDIC SYSTEM FOR RAPID PERSONALIZED DRUG SCREENING AND TESTING METHOD FOR PERSONALIZED ANTIBIOTIC SUSCEPTIBILITY

(71) Applicants: National Tsing Hua University, Hsinchu (TW); Kaohsiung Chang Gung Memorial Hospital, Kaohsiung (TW)

(72) Inventors: Gwo-Bin Lee, Hsinchu (TW); Shiuann-Sheng Lee, Taipei (TW); Wen-Bin Lee, Hsinchu (TW); Huey-Ling You, Kaohsiung (TW)

(73) Assignees: National Tsing Hua University, Hsinchu (TW); Kaohsiung Chang Gung Medical University, Kaohsiung (TW)

( * ) Notice: Subject to any disclaimer, the term of this patent is extended or adjusted under 35 U.S.C. 154(b) by 126 days.

(21) Appl. No.: 16/251,445

(22) Filed: Jan. 18, 2019

(65) Prior Publication Data
US 2020/0230597 A1    Jul. 23, 2020

(51) Int. Cl.
*B01L 3/00* (2006.01)
*C12M 3/00* (2006.01)
(Continued)

(52) U.S. Cl.
CPC ... *B01L 3/502715* (2013.01); *B01L 3/502738* (2013.01); *C12M 23/16* (2013.01); *C12M 29/14* (2013.01); *C12M 41/46* (2013.01); *C12Q 1/18* (2013.01); *G01N 21/78* (2013.01); *G01N 35/00584* (2013.01); *G01N 35/10* (2013.01);
(Continued)

(58) Field of Classification Search
CPC ............. B01L 2400/0481; B01L 2400/0638
See application file for complete search history.

(56) References Cited

U.S. PATENT DOCUMENTS

| | | | | |
|---|---|---|---|---|
| 3,148,624 A | * | 9/1964 | Baldwin | F04B 43/086 417/339 |
| 5,593,290 A | * | 1/1997 | Greisch | F04B 43/021 417/478 |
| 2004/0132218 A1 | * | 7/2004 | Ho | B01L 3/502738 436/524 |

(Continued)

OTHER PUBLICATIONS

Lee et al., "Automatic and rapid antimicrobial susceptibility test on an integrated microfluidic device", The 31st IEEE International Conference on Micro Electro Mechanical Systems (MEMS 2018), 2018, pp. 1209-1212.

*Primary Examiner* — Nathan A Bowers
(74) *Attorney, Agent, or Firm* — The Webb Law Firm

(57) ABSTRACT

The present disclosure provides an automatic microfluidic system for rapid personalized drug screening including a microfluidic chip. The microfluidic chip includes a fluid storage unit, a fluid driving unit, a reaction unit and a plurality of valve units. The fluid driving unit includes two mixing pumps. Each of the mixing pumps includes two pneumatic micro-pumps, a mixing chamber and a blocking structure. The blocking structure is disposed in the mixing chamber and is connected between the two pneumatic micro-pumps. When the two pneumatic micro-pumps are started alternately, the blocking structure is deflected alone with the operation of the two pneumatic micro-pumps.

10 Claims, 15 Drawing Sheets
(2 of 15 Drawing Sheet(s) Filed in Color)

(51) Int. Cl.
*G01N 35/10* (2006.01)
*G01N 21/78* (2006.01)
*G01N 35/00* (2006.01)
*C12M 3/06* (2006.01)
*C12M 1/00* (2006.01)
*C12M 1/34* (2006.01)
*C12Q 1/18* (2006.01)

(52) U.S. Cl.
CPC ............... *B01L 2300/0809* (2013.01); *B01L 2300/0887* (2013.01); *B01L 2300/123* (2013.01); *B01L 2300/18* (2013.01); *B01L 2400/0487* (2013.01); *B01L 2400/06* (2013.01); *G01N 2035/0097* (2013.01); *G01N 2035/00237* (2013.01); *G01N 2035/00247* (2013.01); *G01N 2035/00544* (2013.01)

(56) References Cited

U.S. PATENT DOCUMENTS

| | | | |
|---|---|---|---|
| 2006/0154341 A1* | 7/2006 | Chen | B01L 7/52 435/91.2 |
| 2009/0068700 A1* | 3/2009 | Wikswo | G01N 33/5005 435/29 |
| 2009/0221073 A1* | 9/2009 | Toner | B01L 3/502738 435/378 |
| 2010/0304494 A1* | 12/2010 | Tokhtuev | B01L 3/50273 436/100 |
| 2014/0339266 A1* | 11/2014 | Laflamme | B05B 11/3033 222/207 |
| 2015/0298129 A1* | 10/2015 | Dugan | B01L 3/50851 435/286.1 |
| 2016/0194588 A1* | 7/2016 | Guenat | C12M 35/08 435/305.1 |
| 2018/0088141 A1* | 3/2018 | Vacic | G01N 35/1065 |

* cited by examiner

AUTOMATIC MICROFLUIDIC SYSTEM FOR RAPID PERSONALIZED DRUG SCREENING AND TESTING METHOD FOR PERSONALIZED ANTIBIOTIC SUSCEPTIBILITY

BACKGROUND

Technical Field

The present disclosure relates to a microfluidic system. More particularly, the present disclosure relates to an automatic microfluidic system for rapid personalized drug screening and testing method for personalized antibiotic susceptibility.

Description of Related Art

Antibiotics have been used for 50 years since the discovery of the last century. However, how to use antibiotics correctly is still an important issue for the medical community. Before conventional antibiotics are applied, an antimicrobial susceptibility testing (AST) and the minimum inhibitory concentration (MIC) are the most clinically used methods to assess the efficacy of the antibiotics on bacteria strains present in the patient for achieving the best therapeutic effect.

The current protocol for the antibiotic susceptibility testing includes disk-diffusion test, minimum inhibitory concentration (MIC), minimum bactericidal concentration (MBC), checkboard test, time-kill curves test, and so on. With the development of the medical research, a gene sequence analysis is also applied to detect the antibiotic-resistant bacteria for clinical use. However, the conventional method of the antibiotic susceptibility testing is a time-consuming process and complicated. Furthermore, the sensitivity data of a specific bacteria strain for a specific antibiotic must be determined by a professional after the testing. Thus, the conventional antibiotic susceptibility testing is not common in clinical applications, and its accuracy is not as good as expected.

In order to solve the aforementioned issue, a fully automated detection system for bloodstream infection is provided on the market for simplifying the detection and increasing the accuracy of the detection. However, the instrument and consumables are often costly and often limited to large medical centers, such that not all medical institutions have the capacity to afford.

Accordingly, how to develop an accurate, fast and relatively low cost personalized antibiotic screening system has become an important issue of relevant academic and industry research.

SUMMARY

According to one aspect of the present disclosure, an automatic microfluidic system for rapid personalized drug screening includes a microfluidic chip. The microfluidic chip includes a fluid storage unit, a fluid driving unit, a reaction unit and a plurality of valve units. The fluid storage unit includes a plurality of fluid storage chambers for storing, respectively, a bacterial suspension, a culture medium and a first antibiotic solution. The fluid driving unit is communicated and disposed adjacent to the fluid storage unit. The fluid driving unit includes two mixing pumps, and each of the mixing pumps includes two pneumatic micro-pumps, a mixing chamber and a blocking structure. The two pneumatic micro-pumps are arranged side by side. The mixing chamber is stacked at one side of the two pneumatic micro-pumps. The blocking structure is disposed in the mixing chamber and connected between the two pneumatic micro-pumps, wherein the blocking structure is deflected along with an operation of the two pneumatic micro-pumps when the two pneumatic micro-pumps are alternately started. The reaction unit is communicated with the fluid driving unit and includes a plurality of reaction chambers radially distributed around the fluid driving unit, wherein each of the reaction chambers is for storing a reaction solution. The valve units include a plurality of pneumatic micro-valves and a plurality of valve control air holes. The pneumatic micro-valves are disposed between the fluid storage unit and the fluid driving unit, and between the fluid driving unit and the reaction unit. The valve control air holes are for controlling opening and closing of the pneumatic micro-valves. The fluid driving unit is applied for mixing and quantitatively transporting the bacterial suspension, the culture medium and the first antibiotic solution to each of the reaction chambers so as to form the reaction solution.

According to another aspect of the present disclosure, a testing method for personalized antibiotic susceptibility includes the following steps. The automatic microfluidic system for rapid personalized drug screening is provided according to aforementioned aspect. A first transportation step is performed, wherein the first transportation step is for transporting the bacterial suspension, the culture medium and the first antibiotic solution from the fluid storage chambers, separately, to the mixing chamber by the fluid driving unit. Then, a mixing step is performed, wherein the mixing step is for mixing the bacterial suspension, the culture medium and the first antibiotic solution by alternately starting the two pneumatic micro-pumps of each mixing pump. At that time, the blocking structure is deflected along with the operation of the two pneumatic micro-pumps so as to sufficiently mix the bacterial suspension, the culture medium and the first antibiotic solution and then form the reaction solution. A second transportation step is performed, wherein the reaction step is for transporting the reaction solution from the mixing chamber to each of the reaction chambers separately by the fluid driving unit. A reaction step is performed, wherein the reaction step is for reacting the reaction solution for an incubation time. A determination step is performed, wherein the determination step is for analyzing an incubation status of the reaction solution after the incubation time so as to determine an antibiotic susceptibility of a bacterium of the bacterial suspension to the first antibiotic solution.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiments, with reference made to the accompanying drawings as follows.

DETAILED DESCRIPTION

The present disclosure will be further exemplified by the following specific embodiments. However, the readers should understand that the present disclosure should not be limited to these practical details thereof, that is, in some embodiments, these practical details are used to describe how to implement the materials and methods of the present disclosure and are not necessary.

<Automatic Microfluidic System for Rapid Personalized Drug Screening of the Present Disclosure>

The present disclosure provides an automatic microfluidic system for rapid personalized drug screening. The microfluidic system can automatically perform the operations such as manual liquid distribution and antibiotic concentration dilution in the traditional antibiotic susceptibility testing for single antibiotic or antibiotic combinations through two mixing pumps of a fluid driving unit. The transportation and mixing of fluids can be preciously and efficiently proceeded by the integration of pneumatic micro-pumps and pneumatic micro-valves, and the sample cross-contamination resulted from the conventional operation can be further avoided. Furthermore, compared to the conventional testing method, the automatic microfluidic system for rapid personalized drug screening and testing method for personalized antibiotic susceptibility of the present disclosure makes the entire detection process faster, requires less reagent volume, bypasses the manual determination and the usage of expensive equipment, and still can obtain the accurate results. Thus, the automatic microfluidic system for rapid personalized drug screening and testing method for personalized antibiotic susceptibility provided of the present disclosure can screen fast and reduce the labor cost of hospital so as to present an excellent potential on clinical use.

Figure 1:
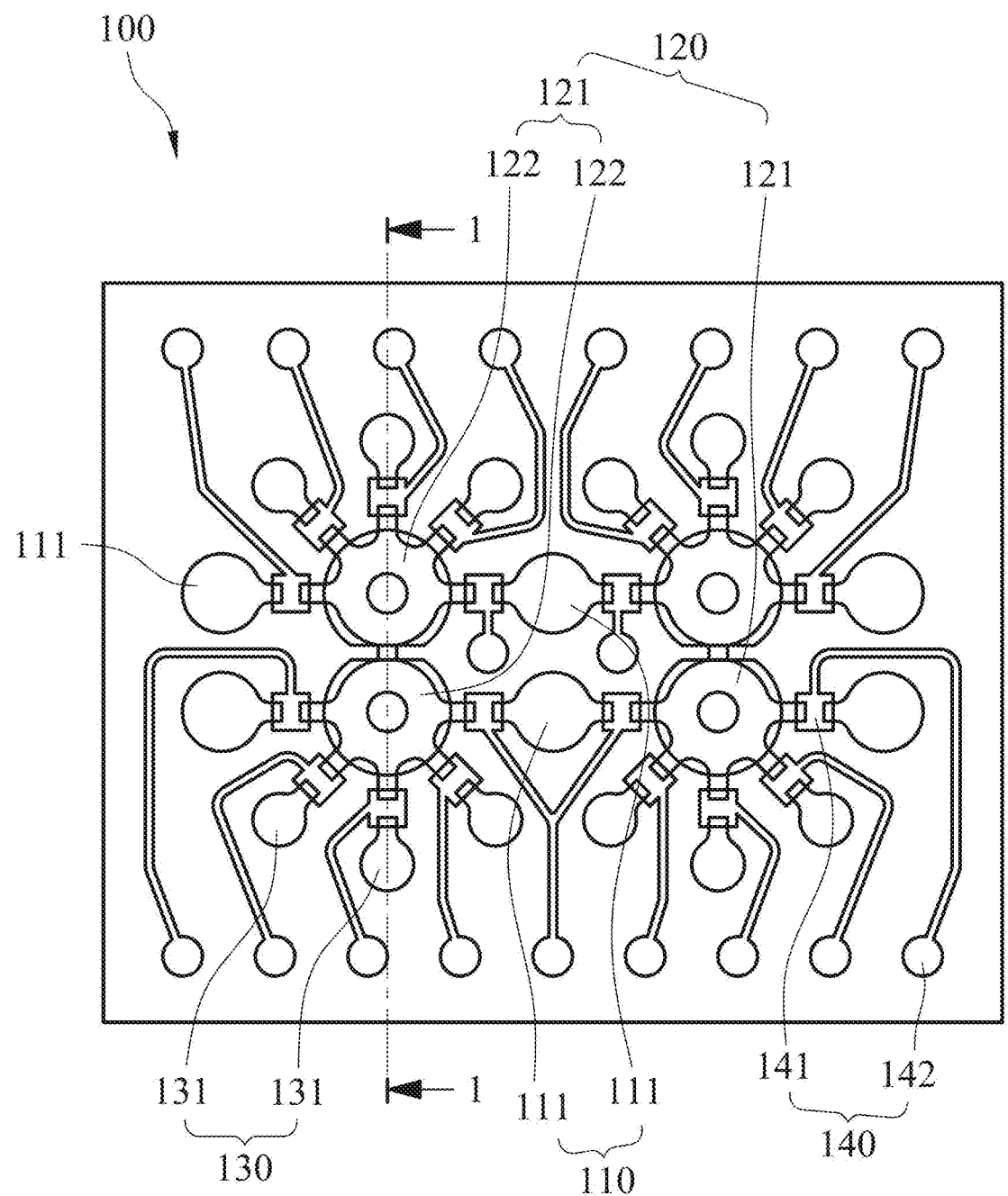
FIG. 1 is a schematic view showing a microfluidic chip according to one example of one embodiment of the present disclosure.
Figure 2:
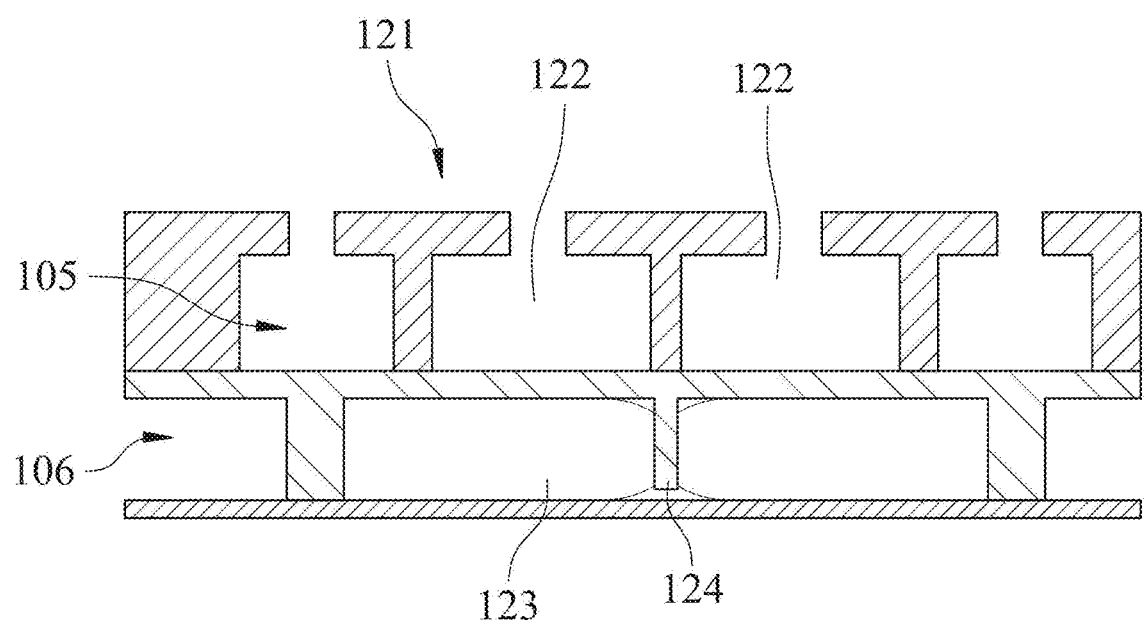
FIG. 2 is a partial cross-sectional view of the microfluidic chip of FIG. 1 along line 1-1.

An automatic microfluidic system (not shown in the figure) for rapid personalized drug screening according to an embodiment of the present disclosure includes a microfluidic chip 100. Please refer to FIG. 1 and FIG. 2, FIG. 1 is a schematic view showing the microfluidic chip 100 according to one example of one embodiment of the present disclosure, and FIG. 2 is a partial cross-sectional view of the microfluidic chip 100 of FIG. 1 along line 1-1. The microfluidic chip 100 includes a fluid storage unit 110, a fluid driving unit 120, a reaction unit 130 and a plurality of valve units 140.

The fluid storage unit 110 includes a plurality of fluid storage chambers 111 for storing, respectively, a bacterial suspension, a culture medium and a first antibiotic solution. In particular, the automatic microfluidic system for rapid personalized drug screening of the present disclosure can be applied for performing a susceptibility testing of a bacterium of the bacterial suspension for various kinds of antibiotics and combination thereof at the same time. Thus, a number of the fluid storage chambers 111 can be arranged according to actual needs. Preferably, the automatic microfluidic system for rapid personalized drug screening of the present disclosure can further include a second antibiotic solution and a third antibiotic solution. Each of the second antibiotic solution and the third antibiotic solution is stored, separately, in one of the fluid storage chambers. In detail, when an antibiotic susceptibility testing of a bacterium present in the bacterial suspension is performed for three or more than three antibiotics and combination thereof at the same time, the number of the fluid storage chambers 111 can be five or more for needs. The five fluid storage chambers 111 are provided for storing, respectively, the bacterial suspension, the culture medium, the first antibiotic solution, the second antibiotic solution and the third antibiotic solution so as to automatically perform the antibiotic susceptibility testing of single bacteria strain for various kinds of antibiotics and combination thereof. The number of the fluid storage chambers 111 is not limited to the aforementioned description and figures. Accordingly, the convenience and application depth of the automatic microfluidic system provided in the present disclosure can be greatly improved.

It must be noted that, except for the first antibiotic solution, the second antibiotic solution and the third antibiotic solution, the automatic microfluidic system for rapid personalized drug screening can further include a fourth antibiotic solution, a fifth antibiotic solution or a variety of different types of antibiotic solutions for needs. Thus, a single antibiotic susceptibility testing or a combined antibiotic susceptibility testing for a variety of different types of antibiotics can be performed at the same time. However, the present disclosure is not limited thereto.

The fluid driving unit 120 is communicated and disposed adjacent to the fluid storage unit 110. The fluid driving unit 120 includes two mixing pumps 121, and each of the mixing pumps 121 includes two pneumatic micro-pumps 122, a mixing chamber 123 and a blocking structure 124. The two pneumatic micro-pumps 122 are arranged side by side. The mixing chamber 123 is stacked at one side of the two pneumatic micro-pumps 122. The blocking structure 124 is disposed in the mixing chamber 123 and connected between the two pneumatic micro-pumps 122. When the two pneumatic micro-pumps 122 are alternately started, the blocking structure 124 is deflected along with the operation of the two pneumatic micro-pumps 122. In detail, the blocking structure 124 is disposed in a liquid channel layer 106 of the microfluidic chip 100 (the structure of the liquid channel layer 106 will be illustrated in the following). When the two pneumatic micro-pumps 122 are alternately started, the blocking structure 124 is extruded by the two pneumatic micro-pumps alternately so as to be deflected and function as a stirrer in the mixing chamber 123. Thus, the mixing of reagents, such as the bacterial suspension, the culture medium and the first antibiotic solution, can be improved. That is, the automatic microfluidic system for rapid personalized drug screening of the present disclosure can greatly improve the mixing efficiency of the fluids and allow the personalized antibiotic susceptibility testing to be more accurate. Furthermore, because the blocking structure 124 is connected between the two pneumatic micro-pumps 122, the surface tension of the fluid in the mixing chamber 123 can be improved and then the suction force, which is resulted from the operation of the two pneumatic micro-pumps 122, can be prevented from over high for maintaining the accuracy of quantitative extraction. Also, the accumulation of the dead volume can be efficiently avoided for maintaining the accuracy of the personalized antibiotic susceptibility. Preferably, two of the fluid storage chambers 111 can be disposed between the two mixing pumps 121 as shown in FIG. 1 for improving fluid transportation efficiency. However, the present disclosure is not limited thereto.

The reaction unit 130 is communicated with the fluid driving unit 120 and includes a plurality of reaction chambers 131. The reaction chambers 131 are radially distributed around the fluid driving unit 120, wherein each of the reaction chambers 131 is for storing a reaction solution. In particular, the automatic microfluidic system for rapid personalized drug screening of the present disclosure can be applied for performing a susceptibility testing of a bacterium of the bacterial suspension for various kinds of antibiotics and combination thereof at the same time. Thus, the reaction chambers 131 can be arranged according to actual needs, such as different dilution concentrations and different amounts of the antibiotic. However, the present disclosure is not limited thereto. Accordingly, a chip size of the microfluidic chip 100 can be efficiently reduced, and the dead volume can be minimized.

The valve units 140 include a plurality of pneumatic micro-valves 141 and a plurality of valve control air holes 142. The pneumatic micro-valves 141 are disposed between the fluid storage unit 110 and the fluid driving unit 120, and between the fluid driving unit 120 and the reaction unit 130. The valve control air holes 142 are for controlling opening and closing of the pneumatic micro-valves 141. Preferably, each of the pneumatic micro-valves 141 can be a normally-closed micro-valve. Therefore, it is favorable for avoiding sample cross-contamination during the quick liquid transportation and assisting the pneumatic micro-pumps 122 to transport preciously.

Figure 3:
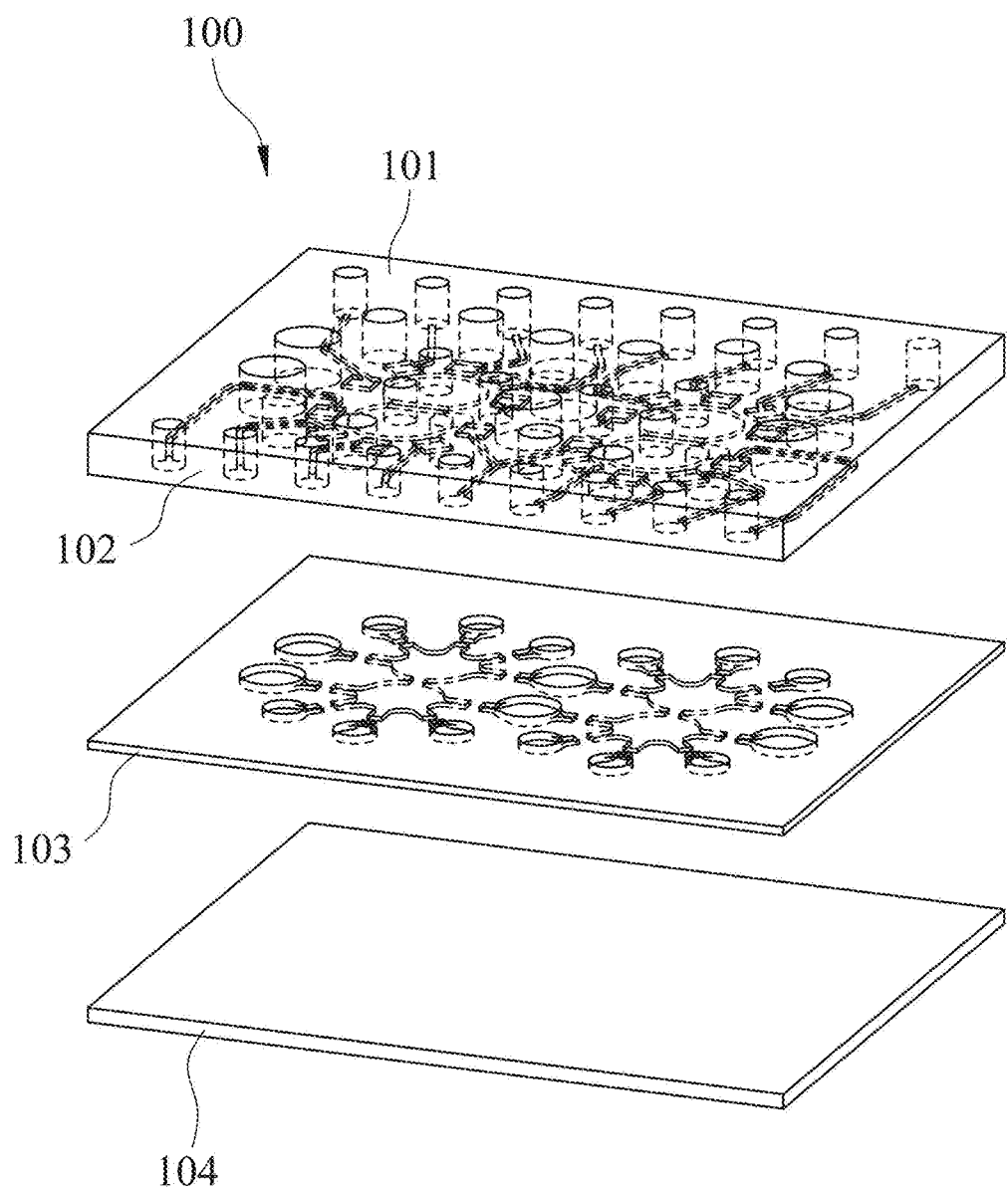
FIG. 3 is an exploded view showing the microfluidic chip of FIG. 1.

Please refer to FIG. 3, which is an exploded view showing the microfluidic chip 100 of FIG. 1. In FIG. 3, the microfluidic chip 100 has a chip surface 101 and includes, in order from the chip surface 101 to a bottom of the microfluidic chip 100, a first flexible base plate 102, a second flexible base plate 103 and a bottom plate 104. The first flexible base plate 102, the second flexible base plate 103 and the bottom plate 104 are stacked in sequence so as to form the fluid storage unit 110, the fluid driving unit 120, the reaction unit 130 and the valve units 140. Preferably, the first flexible base plate 102 and the second flexible base plate 103 are stacked in sequence to form an air channel layer 105, that is, a cavity between the first flexible base plate 102 and the second flexible base plate 103 for transporting air. The second flexible base plate 103 and the bottom plate 104 are stacked in sequence to form the liquid channel layer 106, that is, a cavity between the second flexible base plate 103 and the bottom plate 104 for transporting liquid. The mixing chamber 123 is disposed in the liquid channel layer 106, and the blocking structure 124 is integrally connected with the second flexible base plate 103.

In detail, when the valve control air holes 142 open or close to allow the air entering to or exhausting from the air channel layer 105, the second flexible base plate 103 can be deformed along with the changes of the air volume in the air channel layer 105 due to its flexibility. Thus, the opening and closing of the pneumatic micro-valves 141 can be further controlled. More preferably, the first flexible base plate 102 and the second flexible base plate 103 can be made of poly(dimethylsiloxane), and the bottom plate 104 can be made of glass. Accordingly, the microfluidic chip of the present disclosure has advantages, such as low manufacturing cost, simplified manufacturing process, and mass-producible.

In the following, the operation of the mixing pump 121 of the microfluidic chip 100 of the present disclosure will be illustrated in details with the drawings. Please refer to FIGS. 4A-4F, FIG. 4A is a first operational schematic view of the mixing pump 121 of the microfluidic chip 100 in FIG. 1, FIG. 4B is a second operational schematic view of the mixing pump 121 of the microfluidic chip 100 in FIG. 1, FIG. 4C is a third operational schematic view of the mixing pump 121 of the microfluidic chip 100 in FIG. 1, FIG. 4D is a fourth operational schematic view of the mixing pump 121 of the microfluidic chip 100 in FIG. 1, FIG. 4E is a fifth operational schematic view of the mixing pump 121 of the microfluidic chip 100 in FIG. 1, and FIG. 4F is a sixth operational schematic view of the mixing pump 121 of the microfluidic chip 100 in FIG. 1. The mixing pump 121 of the fluid driving unit 120 utilizes six continuous film movements for transporting and mixing the fluid, wherein FIGS. 4A-4F are illustrated in cooperation with the partial cross-sectional view of FIG. 2. The reference numerals of the members, such as the pneumatic micro-pumps 122 and the pneumatic micro-valves 141 of FIG. 1 and FIG. 2, will be reassigned to be clearly described. Furthermore, FIGS. 4A-4F are diagrams showing a continuous-action process of the mixing pump 121 for fully illustrating the operation of the mixing pump 121.

Figure 4A:
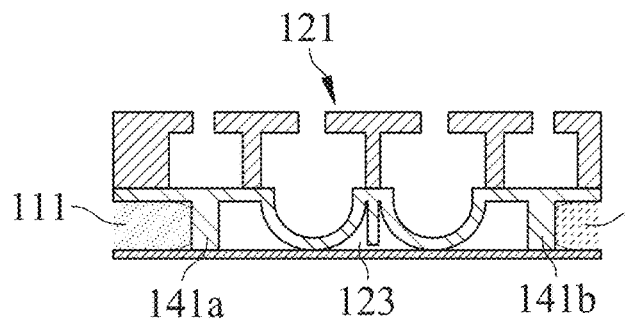
FIG. 4A is a first operational schematic view of a mixing pump of the microfluidic chip in FIG. 1.
Figure 4B:
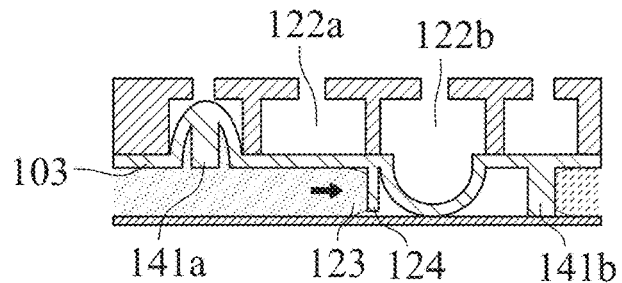
FIG. 4B is a second operational schematic view of a mixing pump of the microfluidic chip in FIG. 1.
Figure 4C:
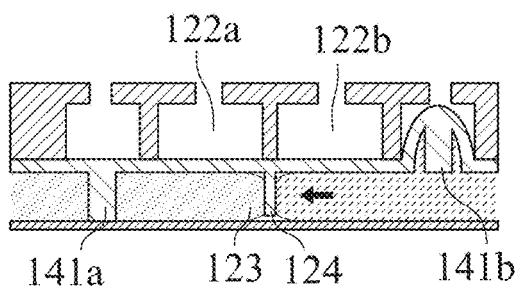
FIG. 4C is a third operational schematic view of a mixing pump of the microfluidic chip in FIG. 1.
Figure 4D:
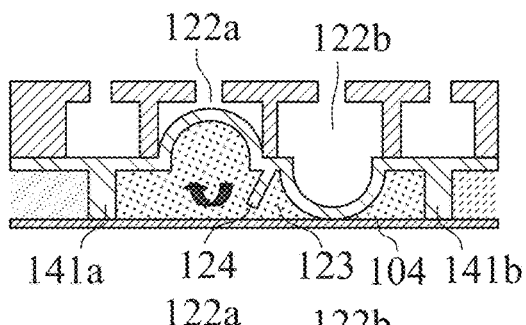
FIG. 4D is a fourth operational schematic view of a mixing pump of the microfluidic chip in FIG. 1.
Figure 4E:
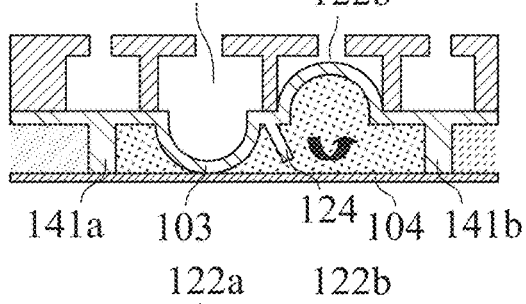
FIG. 4E is a fifth operational schematic view of a mixing pump of the microfluidic chip in FIG. 1.
Figure 4F:
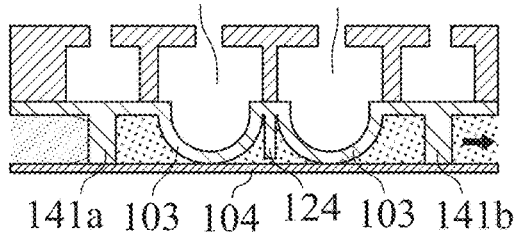
FIG. 4F is a sixth operational schematic view of a mixing pump of the microfluidic chip in FIG. 1.

First, when the pneumatic micro-valve 141a and the pneumatic micro-valve 141b, which are disposed between the mixing pump 121 and the two fluid storage chambers 111, close as shown in FIG. 4A, the fluids of the two fluid storage chambers 111 will be blocked, respectively, by the pneumatic micro-valve 141a and the pneumatic micro-valve 141b so as to be unable to enter the mixing chamber 123.

Next, when the valve control air hole (not shown in the figure), which is communicated with the pneumatic micro-valve 141a, exhausts as shown in FIG. 4B, the second flexible base plate 103, which forms the pneumatic micro-valve 141a, is elevated by a suction force (that is, a negative gauge pressure) caused by vacuum. Then, the fluid stored in one of the fluid storage chambers 111 flows into the mixing chamber 123 and extrudes the second flexible base plate 103, which forms the pneumatic micro-pump 122a, so that the second flexible base plate 103 is elevated. However, the aforementioned fluid will be blocked by the blocking structure 124 disposed in the mixing chamber 123 so as to be limited at one half side of the mixing chamber 123.

Next, when a compressed air (that is, a positive gauge pressure) is supplied through the valve control air hole (not shown in the figure), which is communicated with the pneumatic micro-valve 141a, as shown in FIG. 4C, the second flexible base plate 103, which forms the pneumatic micro-valve 141a, will be extruded by the compressed air to allow the pneumatic micro-valve 141a going down for closing. In the same time, the valve control air hole (not shown in the figure), which is communicated with the pneumatic micro-valve 141b, will exhaust, and the second flexible base plate 103, which forms the pneumatic micro-valve 141b, is then elevated by a suction force caused by vacuum. Thus, it allows the fluid stored in another one of the fluid storage chambers 111 to flow into the mixing chamber 123 for pushing and elevating the second flexible base plate 103, which forms the pneumatic micro-pump 122b. In similar, the fluid transported from another one of the fluid storage chambers 111 will be blocked by the blocking structure 124 disposed in the mixing chamber 123 so as to be limited at another one half side of the mixing chamber 123.

Next, after the fluids of the two fluid storage chambers 111 enter the mixing chamber 123, as shown in FIG. 4D and FIG. 4E, a compressed air is supplied through the valve control air hole (not shown in the figure) communicated with the pneumatic micro-valve 141b, and the second flexible base plate 103, which forms the pneumatic micro-valve 141b, will be extruded by the compressed air to allow the pneumatic micro-valve 141b going down for closing. Then, the two pneumatic micro-pumps 122 are alternately started to allow the second flexible base plate 103, which forms the pneumatic micro-pump 122a and the pneumatic micro-pump 122b, to be deformed alternately by the extrusion of the compressed air and going downward to contact with the bottom plate 104. Thus, the fluids located, respectively, in two half portions of the mixing chamber 123, will be extruded to one another portion of the mixing chamber 123. At that time, the blocking structure 124 will be deflected by the alternate extrusion of the pneumatic micro-pump 122a and the pneumatic micro-pump 122b for mixing the fluids transported from the two fluid storage chambers 111 so as to form the reaction solution.

Finally, in FIG. 4F, the second flexible base plate 103, which forms the pneumatic micro-pump 122a and the pneumatic micro-pump 122b, is extruded by the compressed air and goes downward to contact with the bottom plate 104 at the same time. Thus, the reaction solution will be exhausted through the pneumatic micro-valve 141b and transported to a specific reaction chamber 131.

Through the aforementioned operation, the two mixing pumps 121 of the microfluidic chip 100 of the present disclosure can mix the fluids in a short time and efficiently reduce the accumulation of the dead volume during the mixing process of the fluids.

Furthermore, in some examples, the automatic microfluidic system (not shown in the figure) for rapid personalized drug screening of the present disclosure can further include a temperature control apparatus (not shown in the figure). The temperature control apparatus is stacked with the microfluidic chip 100 for controlling the temperature of the microfluidic chip 100 within a predetermined range. In detail, the predetermined range can be an optimized growing temperature range or other user-defined temperature range so as to be beneficial to the testing.

Furthermore, in some examples, the culture medium can further include an oxidation-reduction indicator (not shown in the figure), and the automatic microfluidic system for rapid personalized drug screening of the present disclosure can further include an absorbance detection device. The absorbance detection device is for detecting an absorbance or a fluorescent value of the reaction solution after an incubation time. In detail, the oxidation-reduction indicator can be used for detecting the changes of the redox state resulted from the metabolism of bacterial growth so that the color change of the reaction solution will occur according to the aforementioned changes of the redox state. Thus, the absorbance detection device can detect an absorbance or a fluorescent value of the reaction solution so as to determine the status of bacterial growth and a minimum inhibitory concentration for a specific antibiotic. Accordingly, the growth status of the bacteria can be determined by the color changes of the reaction solution, and the conventional method for determining the minimum inhibitory concentration, such as the fluorescent staining and an additional microscopy, can be replaced. It is favorable for simplifying the operation of the conventional antibiotic susceptibility testing efficiently and human errors thereof can be avoided. Preferably, the oxidation-reduction indicator can be resazurin.

<Testing Method for Antibiotic Susceptibility of the Present Disclosure>

Figure 5:
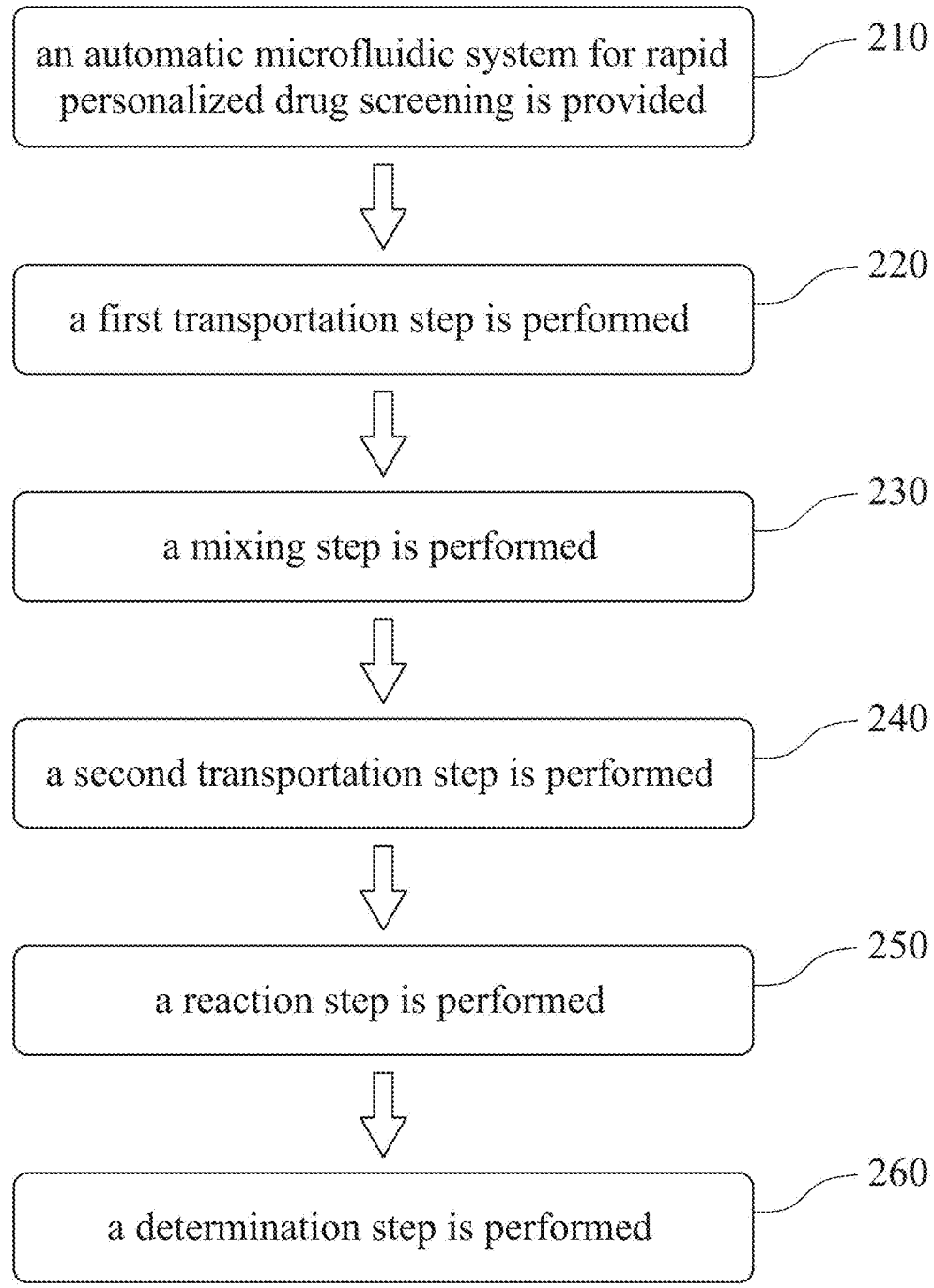
FIG. 5 is a flow chart showing a testing method for personalized antibiotic susceptibility according to one example of another embodiment of the present disclosure.

Please refer to FIG. 5, which is a flow chart showing a testing method 200 for personalized antibiotic susceptibility according to one example of another embodiment of the present disclosure. The testing method 200 for personalized antibiotic susceptibility includes Step 210, Step 220, Step 230, Step 240, Step 250 and Step 260.

In Step 210, an automatic microfluidic system for rapid personalized drug screening is provided. In particular, the automatic microfluidic system for rapid personalized drug screening is the same as mentioned above. The testing method 200 for personalized antibiotic susceptibility of FIG. 5 will be described in cooperation with the aforementioned automatic microfluidic system for rapid personalized drug screening of the present disclosure.

In Step 220, a first transportation step is performed, wherein the first transportation step is for transporting the bacterial suspension, the culture medium and the first antibiotic solution from the fluid storage chambers 111, separately, to the mixing chamber 123 by the fluid driving unit 120. Preferably, a single transportation volume of the first transportation can range from 0.5 µL to 30 µL.

In Step 230, a mixing step is performed, wherein the mixing step is for mixing the bacterial suspension, the culture medium and the first antibiotic solution by alternately starting the two pneumatic micro-pumps 122 of each mixing pump 121. At that time, the blocking structure 124 is deflected along with the operation of the two pneumatic micro-pumps 122 so as to sufficiently mix the bacterial suspension, the culture medium and the first antibiotic solution and them form the reaction solution.

In Step 240, a second transportation step is performed, wherein the second transportation step is for transporting the reaction solution from the mixing chamber 123 to each of the reaction chambers 131 separately by the fluid driving unit 120. Preferably, a single transportation volume of the second transportation is ranged from 0.5 µL to 30 µL.

In Step 250, a reaction step is performed, wherein the reaction step is for reacting the reaction solution for an incubation time. Preferably, the reaction step can be performed under a reaction temperature for the incubation time. More preferably, the incubation time can be ranged from 3 hours to 5 hours.

In Step 260, a determination step is performed, wherein the determination step is for analyzing an incubation status of the reaction solution after the incubation time so as to determine an antibiotic susceptibility of a bacterium of the bacterial suspension to the first antibiotic solution. In particular, the automatic microfluidic system for rapid personalized drug screening can further include an absorbance detection device (not shown in the figure). More particularly, the culture medium can include an oxidation-reduction indicator, and the incubation status is a change of the absorbance or the fluorescence value of the reaction solution. Accordingly, the growth status of the bacteria can be determined by the color changes of the reaction solution, and the conventional method for determining the minimum inhibitory concentration, such as the fluorescent staining and an additional microscopy, can be replaced. It is favorable for simplifying the operation of the conventional antibiotic susceptibility testing efficiently and human errors thereof can be avoided. Preferably, the oxidation-reduction indicator can be resazurin.

Furthermore, although the figures are not shown, in some examples, the testing method for personalized antibiotic susceptibility can further include an adjusting step. In the adjusting step, at least one of the culture medium and the first antibiotic solution is transported to the mixing chamber 123 and then transported to each of the reaction chambers 131 by the fluid driving unit 120 for adjusting a ratio of the bacterial suspension to the first antibiotic solution in the reaction solution. In particular, before the reaction step, several serial dilutions of the reaction solution can be performed automatically in the adjusting step for obtaining reaction solutions with different concentrations of the bacterial suspension and the first antibiotic solution. Accordingly, it is favorable for the following testing of antibiotic susceptibility. Preferably, the automatic microfluidic system for rapid personalized drug screening can further include a second antibiotic solution and a third antibiotic solution. Each of the second antibiotic solution and the third antibiotic solution is stored, separately, in one of the fluid storage chambers 111. The adjusting step is performed for transporting the culture medium, the first antibiotic solution, the second antibiotic solution and the third antibiotic solution, separately, to the mixing chamber 123 and then to each of the reaction chambers 131 so as to adjust a ratio of the bacterial suspension to the first antibiotic solution, the second antibiotic solution and the third antibiotic solution in the reaction solution. Thus, it is favorable for performing a susceptibility testing for several kinds of antibiotics and combination thereof.

It must be noted that, in addition to the first antibiotic solution, the second antibiotic solution and the third antibiotic solution, the automatic microfluidic system for rapid personalized drug screening can further include a fourth antibiotic solution, a fifth antibiotic solution or a variety of different types of antibiotic solutions according to actual needs. Thus, a single antibiotic susceptibility testing or a combined antibiotic susceptibility testing for a variety of different types of antibiotics can be performed at the same time. However, the present disclosure is not limited thereto.

Furthermore, although the figures are not shown, in some examples, the testing method for personalized antibiotic susceptibility can further include a valve controlling step, wherein a suction force and a push force are provided by each of the valve control air holes 142 so as to open or close the pneumatic micro-valves 141 respectively communicated thereto. Preferably, a gauge pressure of the suction force can be larger than or equal to 5 kPa and smaller than or equal to 200 kPa, and a gauge pressure of the push force can be preferably larger than or equal to 5 kPa and smaller than or equal to 200 kPa. Thus, the opening and closing of the pneumatic micro-valves 141 can be efficiently controlled by applying the suitable suction force and push force through the testing method for personalized antibiotic susceptibility of the present disclosure. Thus, the suction force, which is resulted from the operation of the two pneumatic micro-pumps 122, can be prevented from over high for maintaining the accuracy of quantitative extraction. Therefore, the accumulation of the dead volume and the sample cross-contamination can be efficiently avoided for improving the accuracy of testing method for personalized antibiotic susceptibility.

<Determination for Single Fluid Transportation Volume of Automatic Microfluidic System for Rapid Personalized Drug Screening of the Present Disclosure>

A determination for single fluid transportation volume of automatic microfluidic system for rapid personalized drug screening of the present disclosure is performed by using the microfluidic chip 100 of FIG. 1 so as to determine the single fluid transportation volume of the fluid, which is transported to each of the reaction chambers 131 (that is, the aforementioned second transportation step) by the fluid driving unit 120 under different gauge pressures of the push force. An applied gauge pressure of the push force for the transportation is 10 kPa in Example 1, an applied gauge pressure of the push force for the transportation is 30 kPa in Example 2, an applied gauge pressure of the push force for the transportation is 50 kPa in Example 3, and an applied gauge pressure of the push force for the transportation is 70 kPa in Example 4 (n=3).

Figure 6:
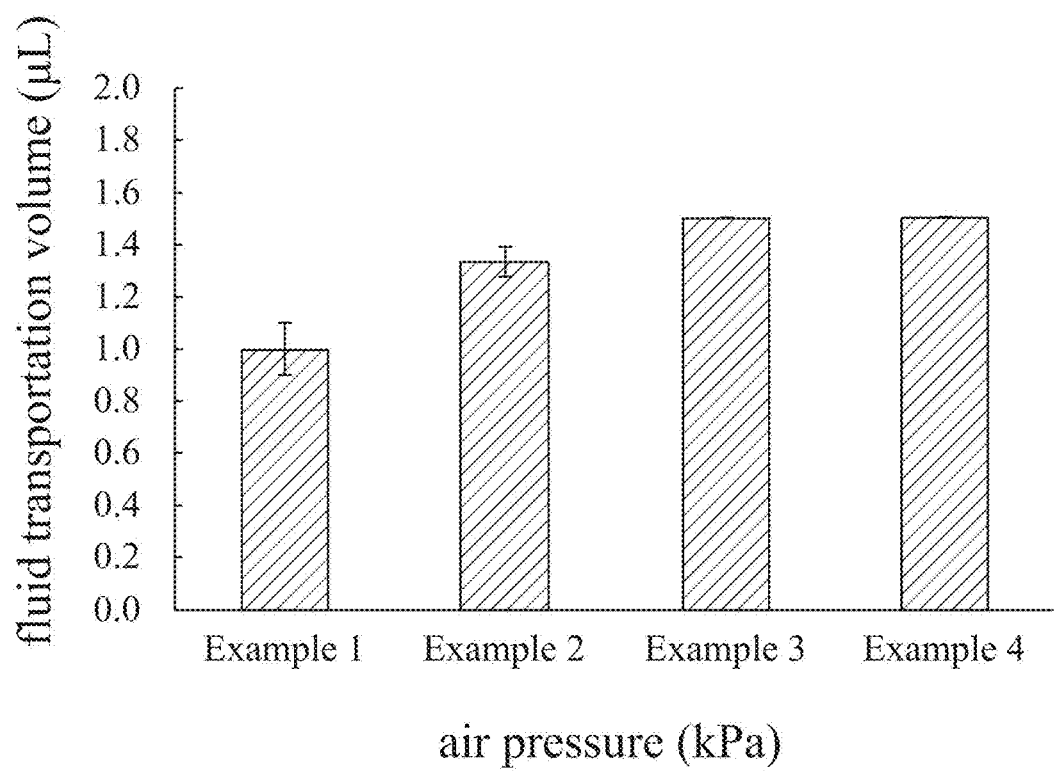
FIG. 6 is a determination result showing single fluid transportation volumes of the microfluidic chip of the present disclosure under different gauge pressures of a push force.

Please refer to FIG. 6, it is a determination result showing single fluid transportation volumes of the microfluidic chip 100 under different gauge pressures of the push force. As shown in FIG. 6, the single fluid transportation volume of Example 1 is 1.0 µL, and the single fluid transportation volume of Example 2 is 1.33 µL. When the gauge pressure of the push force is larger than 50 kPa, as shown in Example 3 and Example 4 of FIG. 6, the single fluid transportation volume of the microfluidic chip 100 of the present disclosure is maintained around 1.5 µL. That is, the single fluid transportation volume of the microfluidic chip 100 of the present disclosure can be controlled by adjusting the magnitude of the gauge pressure of the push force. Furthermore, when the gauge pressure of the push force exceeds a specific value, the single fluid transportation volume thereof can be constant so as to prevent the fluid from rushing in the flow channels and then affecting the accuracy of the antibiotic susceptibility testing.

<Consistency Testing of Single Fluid Transportation Volume of Automatic Microfluidic System for Rapid Personalized Drug Screening of the Present Disclosure>

Figure 7A:
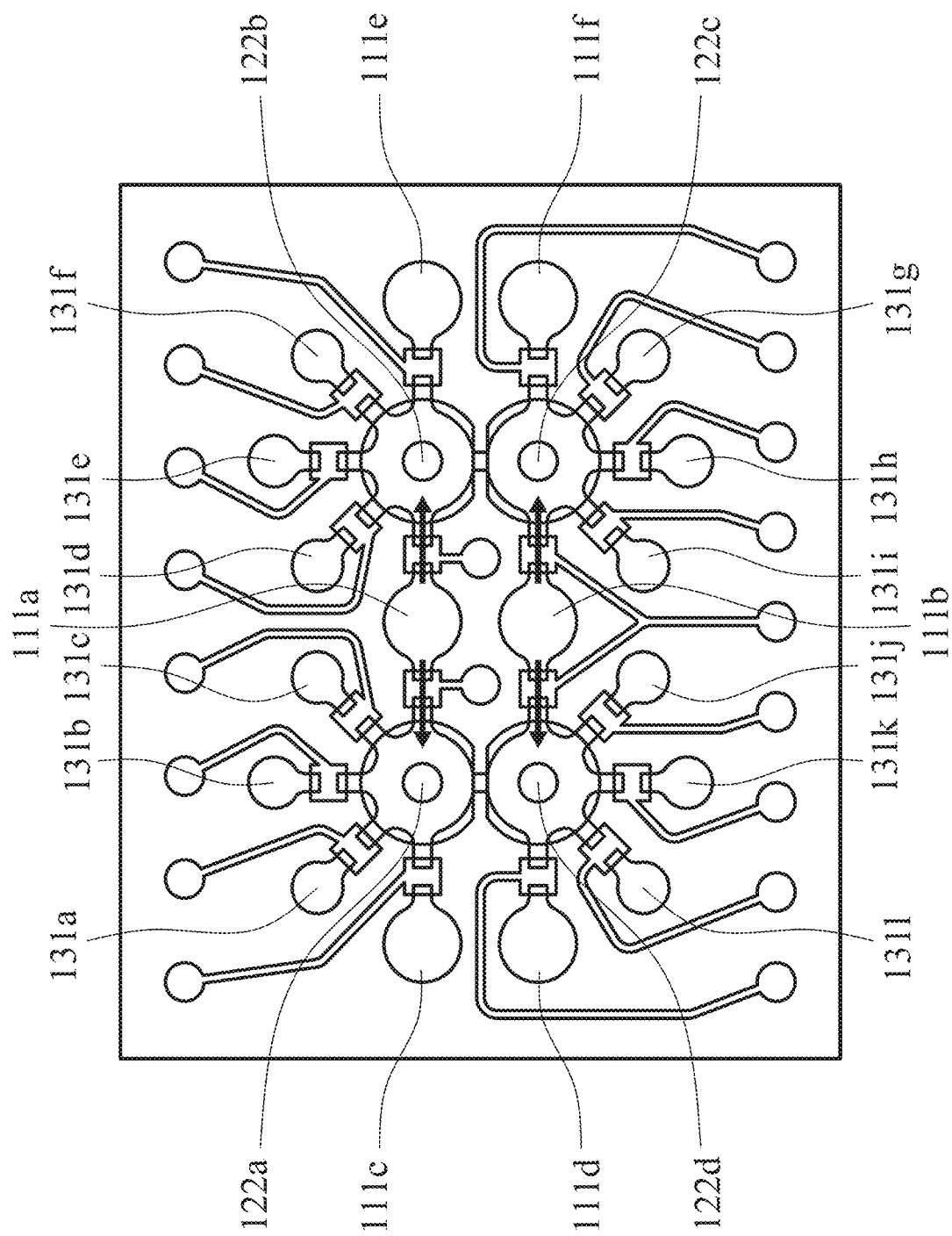
FIG. 7A is a schematic view showing a fluid transportation direction of the microfluidic chip of the present disclosure.

Please refer to FIG. 7A, which is a schematic view showing a fluid transportation direction of the microfluidic chip 100 of the present disclosure. A consistency testing of single fluid transportation volume of automatic microfluidic system for rapid personalized drug screening is performed by using the microfluidic chip 100 of FIG. 7A. When the gauge pressures are the same and the fluids (that is, the distilled water) of the fluid storage chamber 111a and the fluid storage chamber 111b have a positive gauge pressure of 50 kPa and a negative gauge pressure of 70 kPa, the single fluid transportation volumes (n=3) transported, respectively, from the pneumatic micro-pump 122a, the pneumatic micro-pump 122b, the pneumatic micro-pump 122c and the pneumatic micro-pump 122d to the fluid storage chamber 111c, the fluid storage chamber 111d, the fluid storage chamber 111e and the fluid storage chamber 111f and then to the reaction chambers 131a to 131l can be determined.

It must be noted that the microfluidic chip 100 of FIG. 7A is the same as the microfluidic chip 100 of FIG. 1. FIG. 7A is further provided in the present testing in order to illustrate the fluid transportation direction of the present testing and the single fluid transportation volumes received, respectively, by the fluid storage chamber 111c, the fluid storage chamber 111d, the fluid storage chamber 111e and the fluid storage chamber 111f more conveniently. The reference numerals of the members of the microfluidic chip 100 will be reassigned herein, and it is favorable for the following description.

Figure 7B:
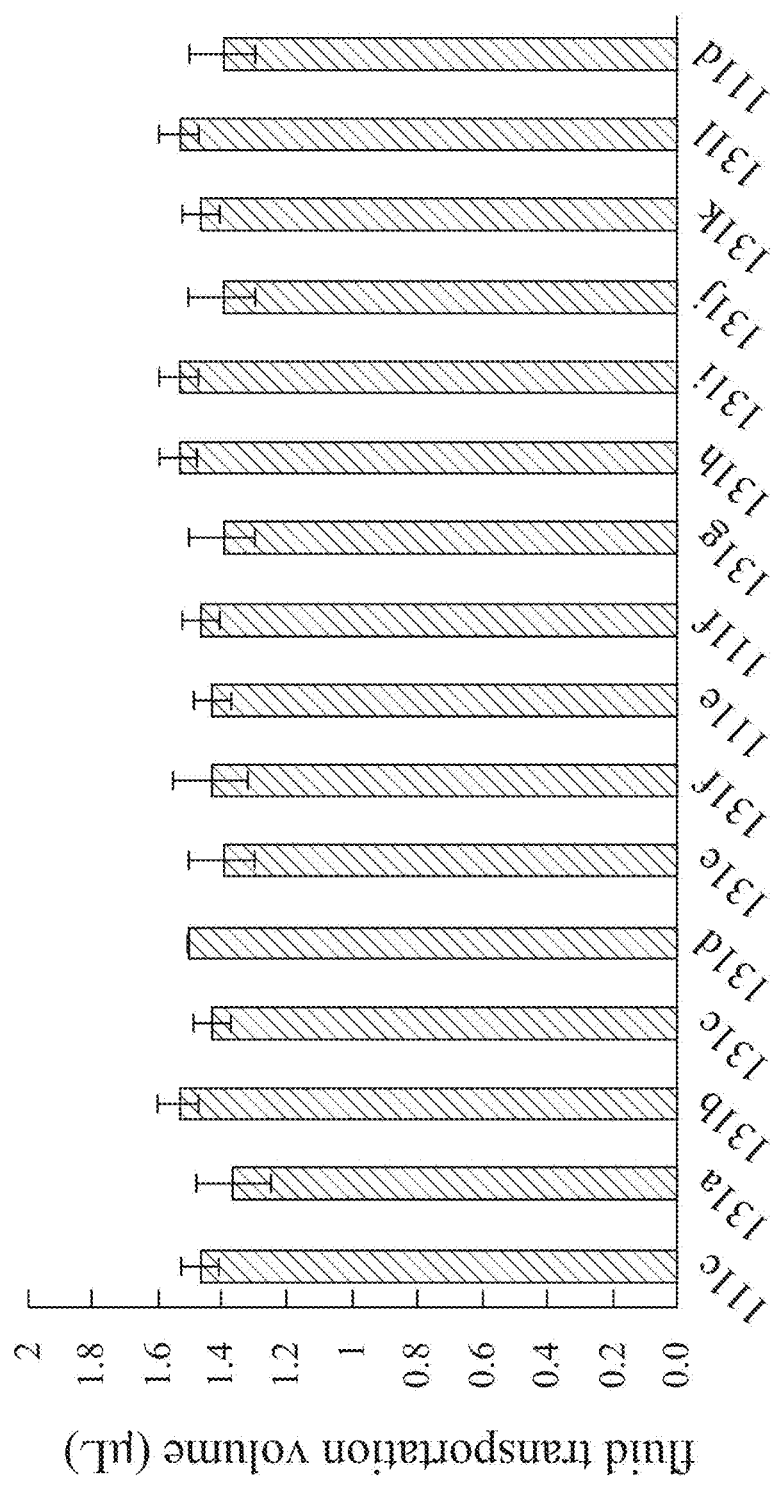
FIG. 7B is a determination result showing single fluid transportation volumes of the microfluidic chip in FIG. 7A.

Please refer to FIG. 7B, which is a determination result showing single fluid transportation volumes of the microfluidic chip 100 in FIG. 7A. In FIG. 7B, the fluids in the fluid storage chamber 111c, the reaction chamber 131a, the reaction chamber 131b and the reaction chamber 131c are transported by the pneumatic micro-pump 122a, and the single fluid transportation volumes thereof all range from 1.0 µL to 1.5 µL. The fluids in the fluid storage chamber 111e, the reaction chamber 131d, the reaction chamber 131e and the reaction chamber 131f are transported by the pneumatic micro-pump 122b, and the single fluid transportation volumes thereof all range from 1.0 µL to 1.5 µL. The fluids in the fluid storage chamber 111f, the reaction chamber 131g, the reaction chamber 131h and the reaction chamber 131i are transported by the pneumatic micro-pump 122c, and the single fluid transportation volumes thereof all ranges from 1.0 µL to 1.5 µL. The fluids in the fluid storage chamber 111d, the reaction chamber 131j, the reaction chamber 131k and the reaction chamber 131l are transported by the pneumatic micro-pump 122d, and the single fluid transportation volumes thereof all ranges from 1.0 µL to 1.5 µL.

As mentioned above, the single fluid transportation volumes of the fluid storage chambers 111c to 111f and the reaction chambers 131a to 131l all range from 1.0 µL to 1.5 µL. That is, the microfluidic chip 100 of the present disclosure has high single fluid transportation volume consistency so as to allow the fluid to be preciously transported to each of the chambers.

<Determination for Mixing Index of Automatic Microfluidic System for Rapid Personalized Drug Screening of the Present Disclosure>

A determination for mixing index of automatic microfluidic system for rapid personalized drug screening of the present disclosure is performed by using the microfluidic chip 100 of FIG. 1. The mixing pump 121 is for mixing an ink and a distilled water located at two sides of the blocking structure 124 in the mixing chamber 123 so as to determine a mixing time of the mixing pump 121 for the fluid under different gauge pressures. In such test, an applied gauge pressure of the push force for mixing is 10 kPa in Example 5, an applied gauge pressure of the push force for mixing is 30 kPa in Example 6, and an applied gauge pressure of the push force for mixing is 50 kPa in Example 7 (n=3).

Figure 8A:
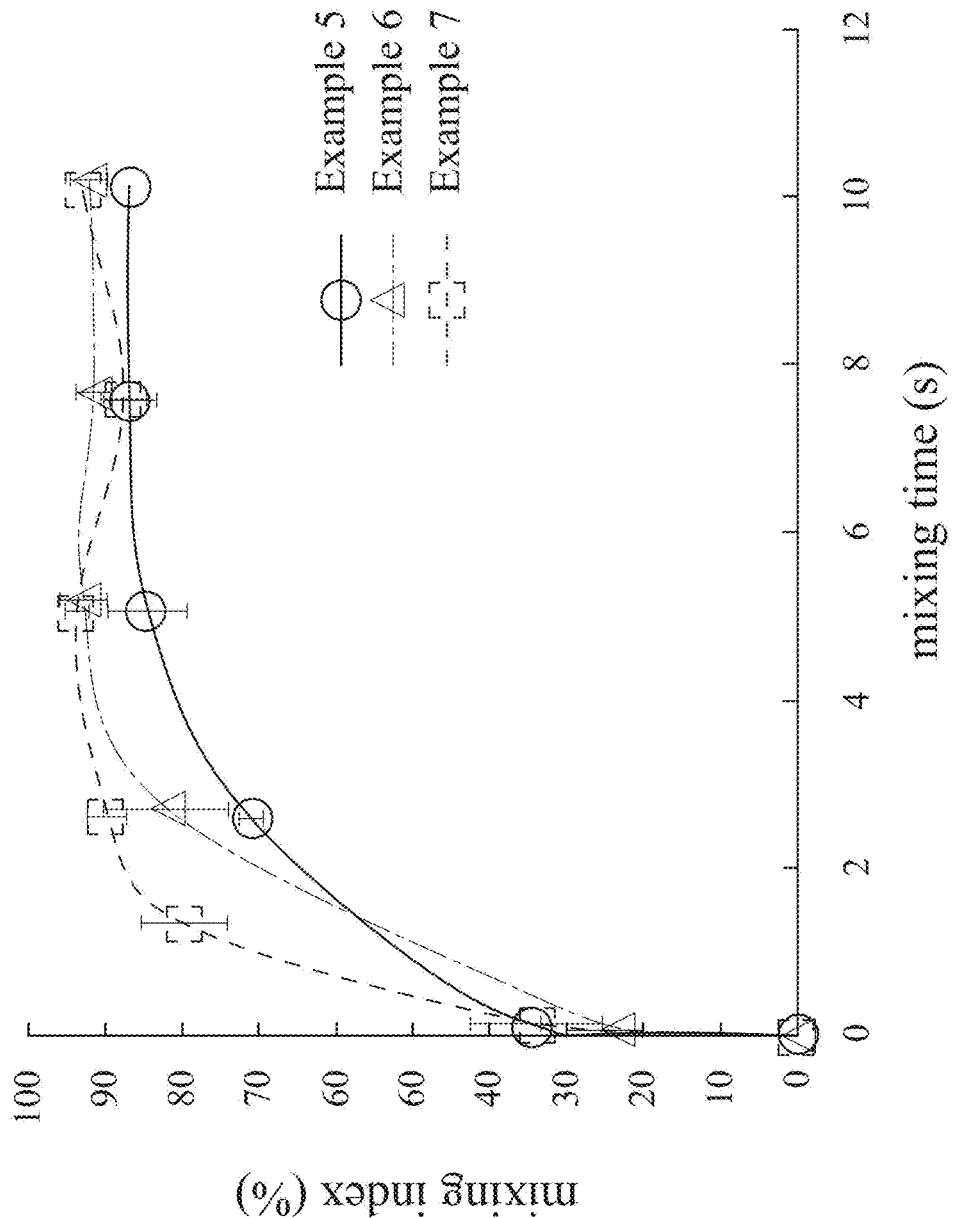
FIG. 8A is a determination result showing mixing indexes of the microfluidic chip of the present disclosure under different gauge pressures of the push force.
Figure 8B:
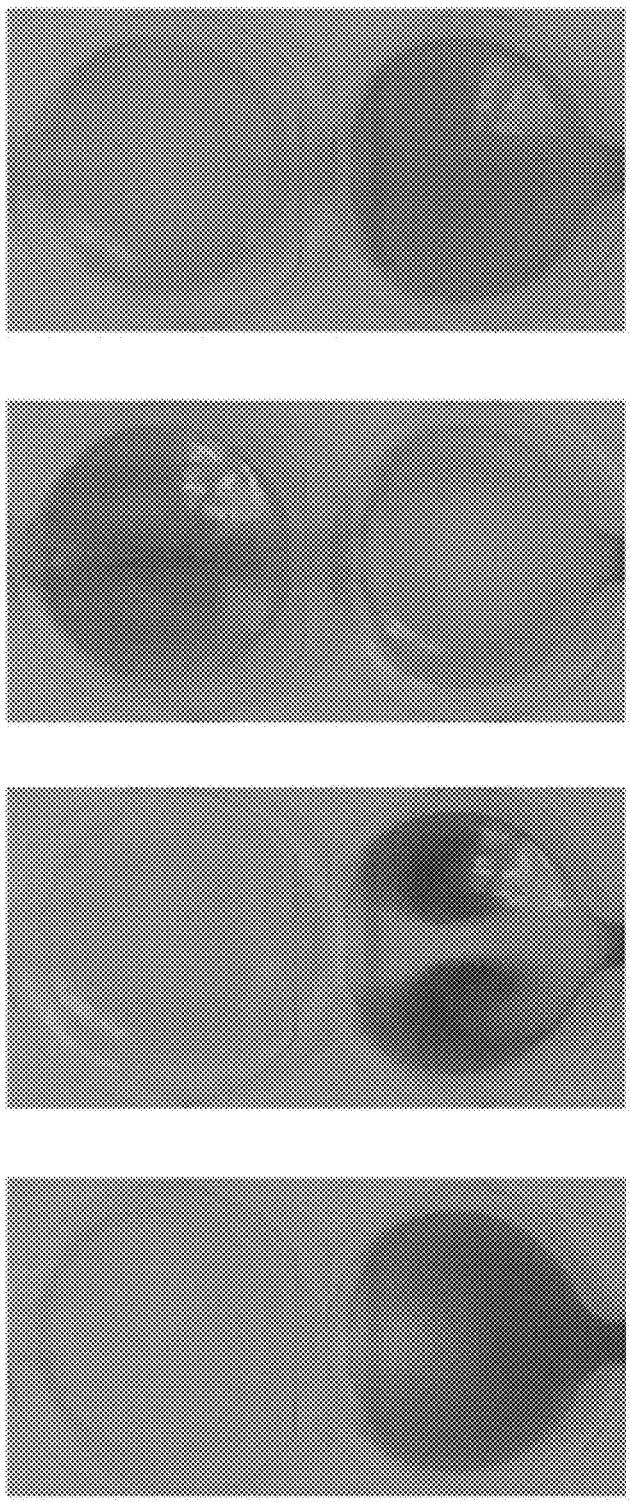
FIG. 8B are images showing a mixing process of an ink and a distilled water under different time period in Example 7.

Please refer to FIG. 8A, which is a determination result showing mixing indexes of the microfluidic chip 100 of the present disclosure under different gauge pressures of the push force. In FIG. 8A, Example 5 can achieve a mixing index of over 80% after mixing for 6 seconds, and Example 6 can achieve a mixing index of over 80% after mixing for 3 seconds. Referring to FIG. 8A and FIG. 8B, FIG. 8B are images showing a mixing process of an ink and a distilled water under different time period in Example 7. In FIG. 8B, the images from left to right are taken after mixing for 1 second, 0.14 second, 1.33 second and 2.6 seconds in Example 7. In Example 7, as shown in FIG. 8A and FIG. 8B, the ink and the distilled water are located, respectively, at two sides of the blocking structure 124 disposed in the mixing chamber 123 in the beginning (that is, 0 second). After mixing for 0.14 second and 1.33 second, a homogeneous status can be gradually achieved. A mixing index of over 90% is even achieved after mixing for 2.6 seconds.

Through the aforementioned operation, the automatic microfluidic system for rapid personalized drug screening of the present disclosure can achieve a good mixing performance of the fluids in a short time, so that the using efficiency thereof can be efficiency enhanced.

<Determination for Dilution Efficiency of Automatic Microfluidic System for Rapid Personalized Drug Screening of the Present Disclosure>

Figure 9A:
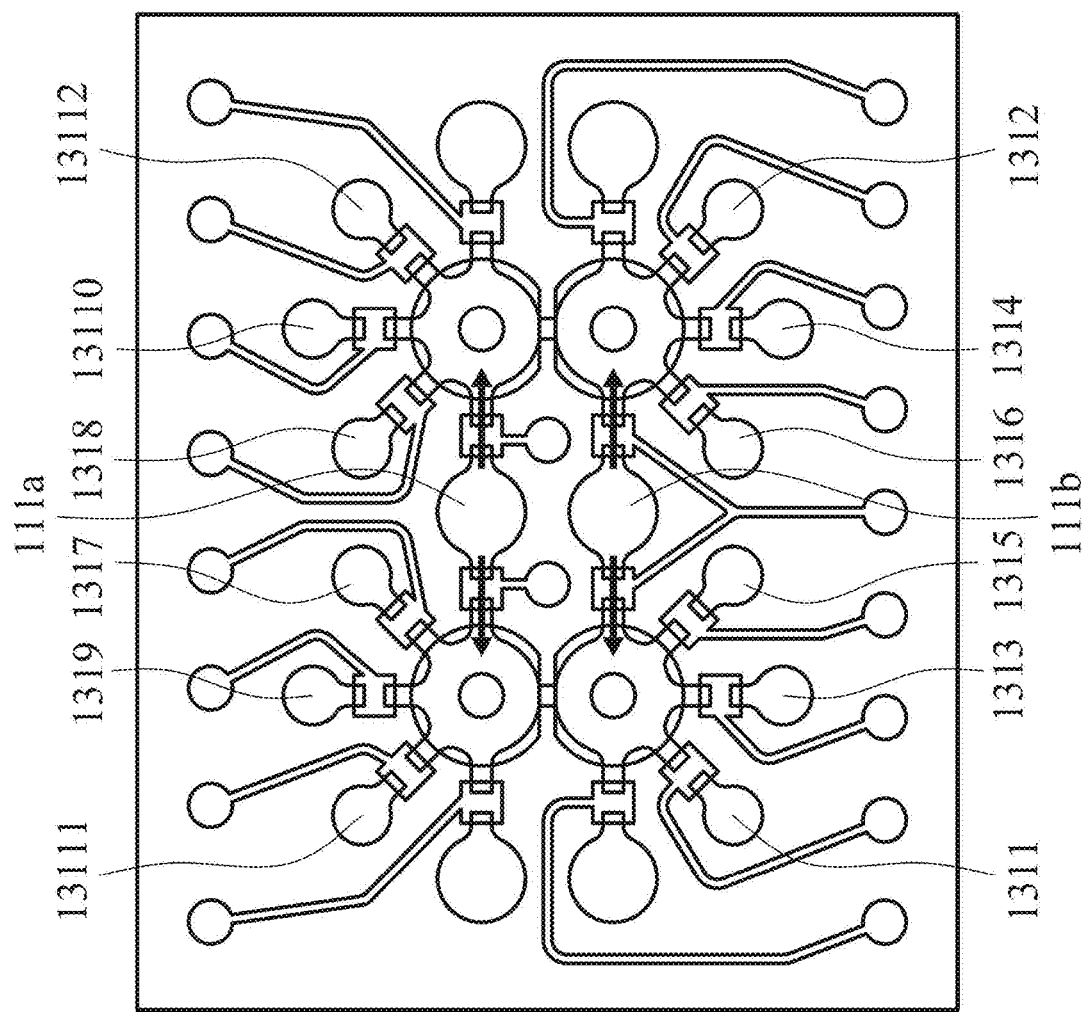
FIG. 9A is another schematic view showing the fluid transportation direction of the microfluidic chip of the present disclosure.

Please refer to FIG. 9A, which is another schematic view showing the fluid transportation direction of the microfluidic chip 100 of the present disclosure. A determination for dilution efficiency of automatic microfluidic system for rapid personalized drug screening of the present disclosure is performed in Example 8 by using the microfluidic chip 100 of FIG. 9A. In Example 8, double-stranded DNA (hereafter referred as dsDNA) stored in the fluid storage chamber 111a is quantitatively diluted by using the distilled water stored in the fluid storage chamber 111b with a two-fold serial dilution mode (n=5). Absorbance of the reaction solutions, which are stored, respectively, in the reaction chambers 131l to 131l2, can be measured at a wavelength of 260 nm by a spectrophotometer, and the amount of dsDNA can be analyzed according to the absorbance.

It must be noted that the microfluidic chip 100 of FIG. 9A is the same as the microfluidic chip 100 of FIG. 1. FIG. 9A is further provided in the present determination in order to illustrate the fluid transportation direction of the present testing and the concentration of the reaction solutions in the reaction chambers 1311-13112. The reference numerals of the members of the microfluidic chip 100 will be reassigned herein, and it is favorable for the following description.

Figure 9B:
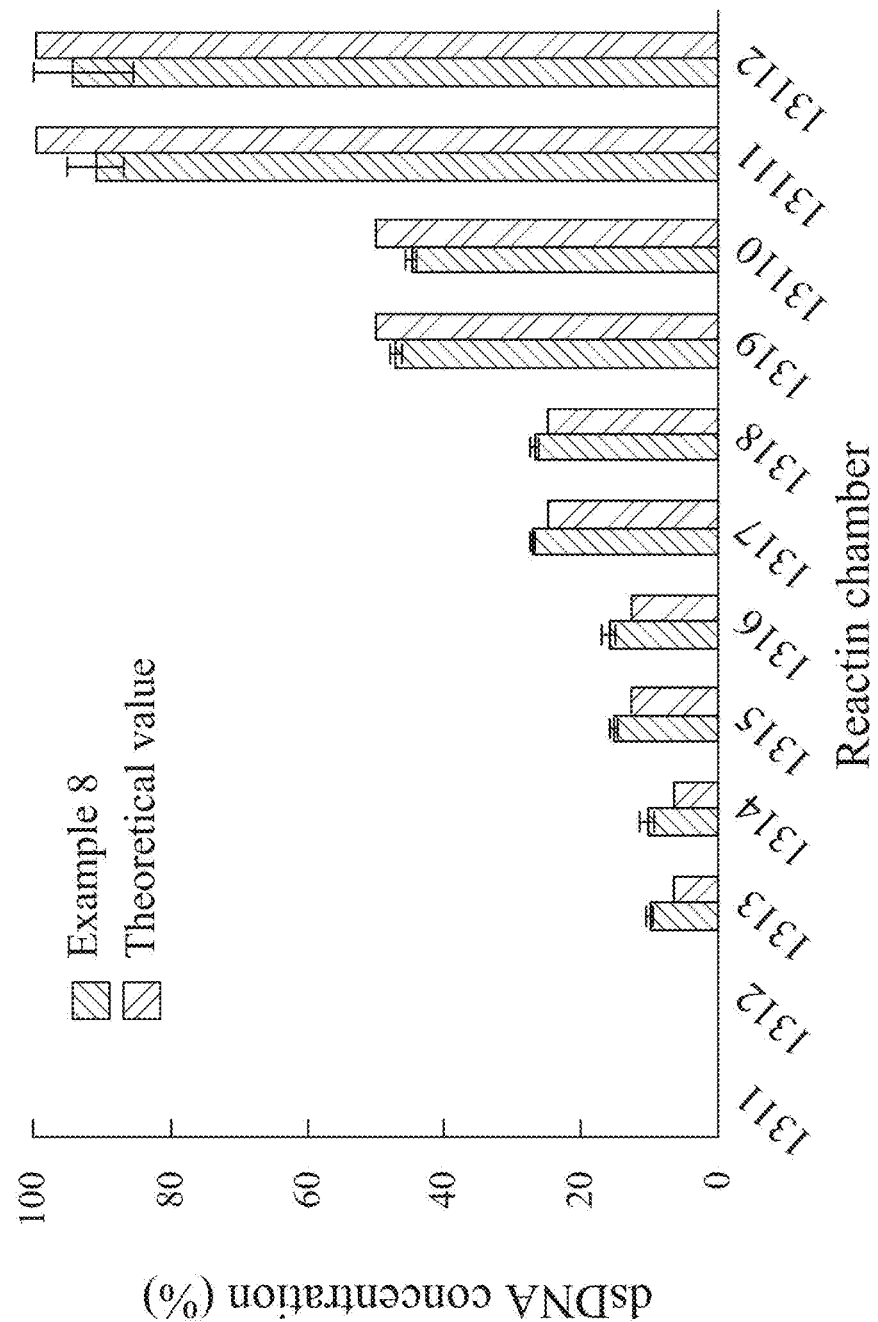
FIG. 9B is a quantitative dilution performance of Example 8.

Please refer to FIG. 9B, which is a quantitative dilution performance of Example 8. In FIG. 9B, the dilution performances show excellent agreement between the automatic microfluidic system for rapid personalized drug screening of the present disclosure and the theoretical value for the dilution of the dsDNA in the two-fold serial dilution mode, and the comparison results all fall within a 95% confidence interval. Thus, the aforementioned data give evidence of the performance of the automatic microfluidic system for rapid personalized drug screening of the present disclosure. Therefore, not only the human errors thereof can be avoided, but the microfluidic system can replace the manual system to perform a quantitative test preciously and automatically.

<Determination of Minimum Inhibitory Concentration by Using Automatic Microfluidic System for Rapid Personalized Drug Screening of the Present Disclosure>

A determination of minimum inhibitory concentration is performed by using the microfluidic chip 100 of FIG. 1 in cooperated with the testing method 200 for personalized antibiotic susceptibility of FIG. 5. The details of the testing method 200 has been described as mentioned above so that the same process will not be further illustrated herein.

For clarity, the reference numerals of the fluid storage chamber 111 and the reaction chamber 131 of the microfluidic chip 100 of FIG. 1 will be reassigned.

[Single Antibiotic Susceptibility Testing]

In Example 9, vancomycin-intermediate *Staphylococcus aureus* (VISA) is designed as a bacterial suspension so as to test the minimum inhibitory concentrations of vancomycin and gentamicin for the vancomycin-intermediate *Staphylococcus aureus* at the same time. Furthermore, the culture medium is stored in the fluid storage chamber 111b and includes resazurin as an oxidation-reduction indicator for determining the bacterial growth of the vancomycin-intermediate *Staphylococcus aureus* through the color changes of the reaction solution.

In experimental, the microfluidic chip 100 is divided into a reaction zone 1001 and a reaction zone 1002 along line 10-10 by using the fluid storage chamber 111a and the fluid storage chamber 111b as a center. The reaction zone 1001 is utilized for determining the minimum inhibitory concentration of vancomycin for the vancomycin-intermediate *Staphylococcus aureus*, and the reaction zone 1002 is utilized for determining the minimum inhibitory concentration of gentamicin for the vancomycin-intermediate *Staphylococcus aureus*. After 4 hours of incubation of the reaction solutions including the resazurin, with different concentrations, the color of the reaction solution will be gradually changed to red when the vancomycin-intermediate *Staphylococcus aureus* grows and can be observed directly through the microfluidic chip 100.

In such the example, the reference numerals of the reaction chambers 131 of the microfluidic chip 100 are reassigned to the reaction chambers 131a to 131l. In the reaction zone 1001, concentrations of the vancomycin in the reaction chamber 131a, the reaction chamber 131b, the reaction chamber 131c, the reaction chamber 131d, the reaction chamber 131e and the reaction chamber 131f are 0 μg/mL, 0.8 μg/mL, 1.20 μg/mL, 2.16 μg/mL, 3.76 μg/mL and 7.28 μg/mL, respectively. In the reaction zone 1002, concentrations of the gentamicin in the reaction chamber 131g, the reaction chamber 131h, the reaction chamber 131i, the reaction chamber 131j, the reaction chamber 131k and the reaction chamber 131l are 0 μg/mL, 0.80 μg/mL, 1.20 μg/mL, 2.16 μg/mL, 3.76 μg/mL and 7.28 μg/mL, respectively. All concentrations of the vancomycin-intermediate *Staphylococcus aureus* in the reaction chambers 131a to 131l are 1500 CFU, and the volume of the reaction solution is 3 μL.

Furthermore, the present testing further includes Comparative Example 1. In Comparative Example 1, a broth microdilution is utilized for determining minimum inhibitory concentrations of vancomycin and gentamicin for the vancomycin-intermediate *Staphylococcus aureus* under the same conditions so as to analyze the accuracy of determining the minimum inhibitory concentration performed by the automatic microfluidic system for rapid personalized drug screening of the present disclosure.

Figure 10:
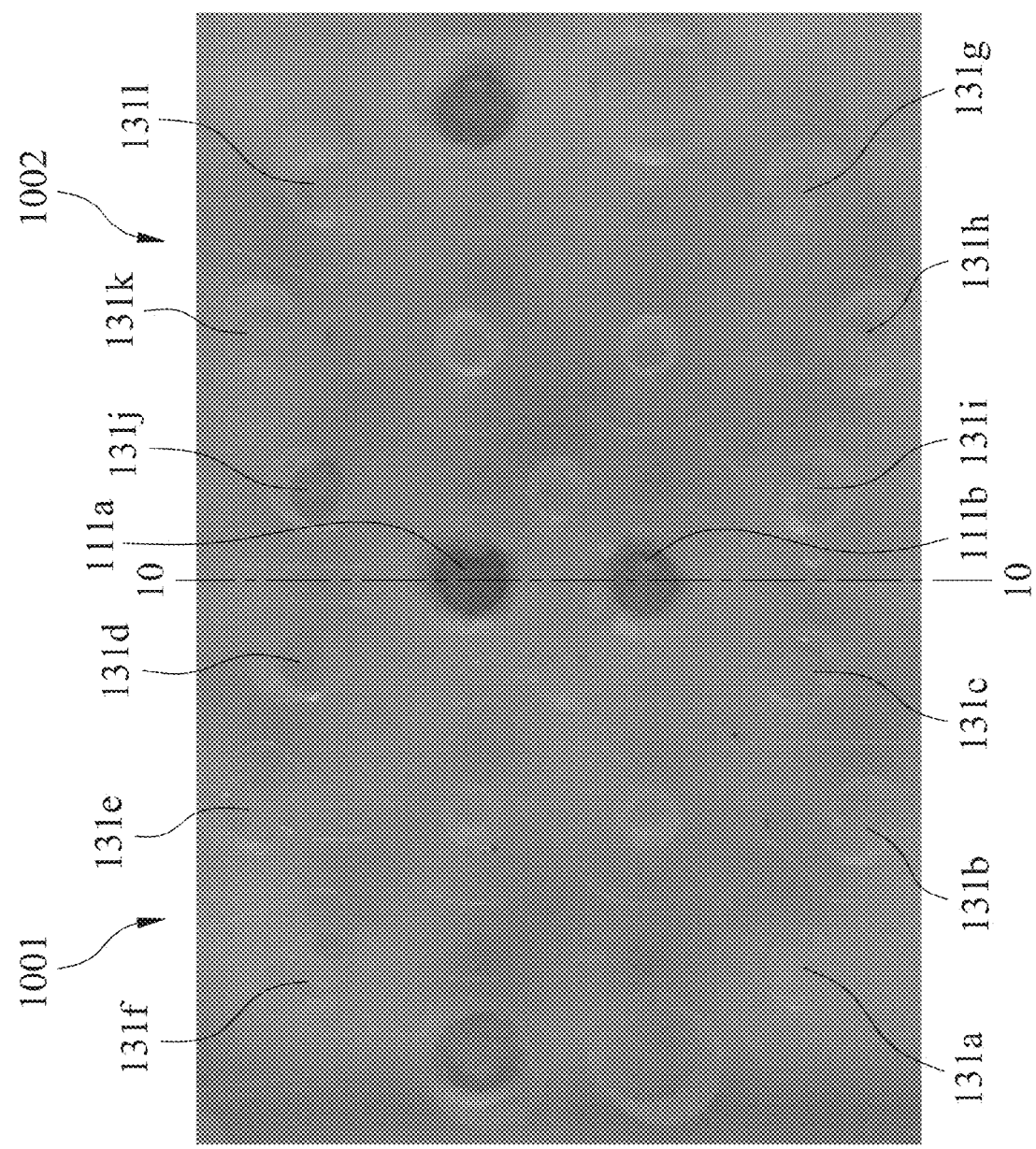
FIG. 10 is colorimetric results of an antibiotic susceptibility testing in Example 9.

Please refer to FIG. 10 and Table 1. FIG. 10 is colorimetric results of an antibiotic susceptibility testing in Example 9, and results of determining the minimum inhibitory concentration in Example 9 and Comparative Example 1 are listed in Table 1.

TABLE 1

| Antibiotic | Example 9 (μg/mL) | Comparative Example 1 (μg/mL) | Difference (%) |
|---|---|---|---|
| Vancomycin | 2.16 | 2 | 8 |
| Gentamicin | >7.52 | >8 | 6 |

As shown in FIG. 10 and Table 1, the determination of the minimum inhibitory concentrations of vancomycin and gentamicin for the vancomycin-intermediate *Staphylococcus aureus*, which is performed by the automatic microfluidic system for rapid personalized drug screening provided in the present disclosure, obtains the same result with the determination of the minimum inhibitory concentrations performed by Comparative Example 1. That is, the automatic microfluidic system for rapid personalized drug screening can automatically perform the antibiotic susceptibility testing for the bacteria, and the determination results can be visually observed. Thus, the cost and time of the antibiotic susceptibility testing can be reduced so as to present a potential for clinical use.

[Personalized Antibiotic Combination Susceptibility Testing]

In Example 10, vancomycin-intermediate *Staphylococcus aureus* (VISA) is designed as a bacterial suspension to be tested for determining minimum inhibitory concentrations of various combinations of vancomycin, gentamicin and ceftazidime for the vancomycin-intermediate *Staphylococcus aureus* at the same time. The testing method of Example 10 is actually the same as Example 9, and thus the details will not be described herein. In addition, the culture medium is stored in the fluid storage chamber 111b and also includes resazurin as the oxidation-reduction indicator for determining the bacterial growth of the vancomycin-intermediate *Staphylococcus aureus* through the color changes of the reaction solution. According to the definition for the interaction between the antibiotics and the analysis for the intensity of red color scale, the aforementioned antibiotic combination will be considered as synergistic activity for the vancomycin-intermediate *Staphylococcus aureus* when the reaction solution is applied with the antibiotic combination and has a color closer to blue-purple than the color in the case of single antibiotic. Otherwise, the aforementioned antibiotic combination will be considered as antagonistic activity for the vancomycin-intermediate *Staphylococcus aureus* when the reaction solution is applied with the antibiotic combination and has a color closer to red than the color in the case of single antibiotic.

In the present example, the reference numerals of the reaction chamber 131 of the microfluidic chip 100 will be reassigned from the reaction chamber 131a to the reaction chamber 131j. Concentration ratios of the antibiotics in the reaction chambers 131a-131j are listed in Table 2.

TABLE 2

| Reaction chamber | Vancomycin (%) | Gentamicin (%) | Ceftazidime (%) |
|---|---|---|---|
| 131a | 50 | 25 | 12.5 |
| 131b | 25 | 12.5 | 50 |
| 131c | 12.5 | 50 | 25 |
| 131d | 50 | 50 | 0 |
| 131e | 50 | 0 | 50 |
| 131f | 0 | 50 | 50 |
| 131g | 100 | 0 | 0 |
| 131h | 0 | 100 | 0 |

TABLE 2-continued

| Reaction chamber | Vancomycin (%) | Gentamicin (%) | Ceftazidime (%) |
|---|---|---|---|
| 131i | 0 | 0 | 100 |
| 131j | 0 | 0 | 0 |

Furthermore, the present testing further includes a Comparative Example 2. In Comparative Example 2, a broth microdilution is utilized for determining minimum inhibitory concentrations of vancomycin, gentamicin and ceftazidime for the vancomycin-intermediate *Staphylococcus aureus* under the same conditions so as to analyze the accuracy of determining the minimum inhibitory concentration performed by the automatic microfluidic system for rapid personalized drug screening of the present disclosure.

Figure 11A:
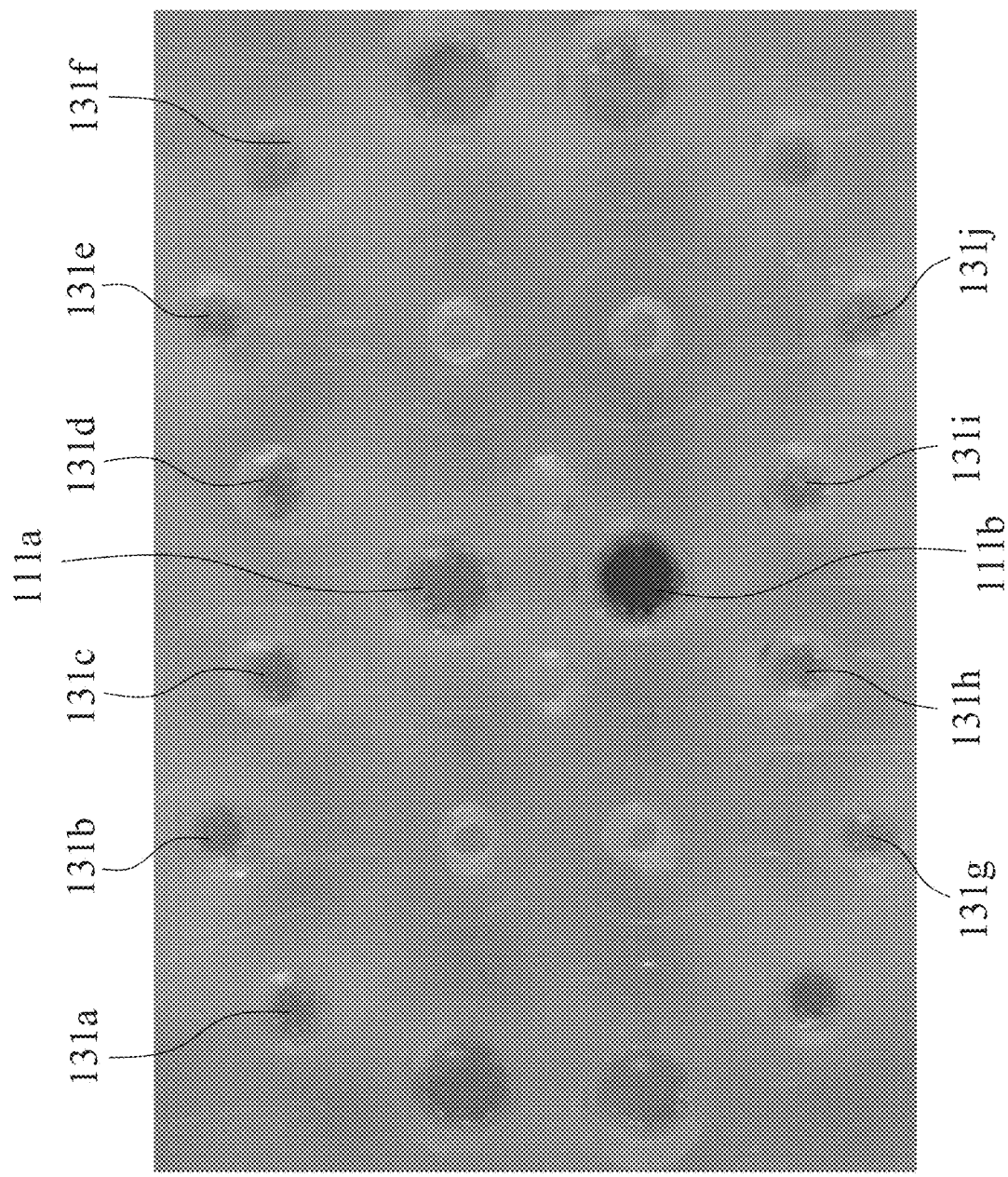
FIG. 11A is colorimetric results of an antibiotic susceptibility testing in Example 10.
Figure 11B:
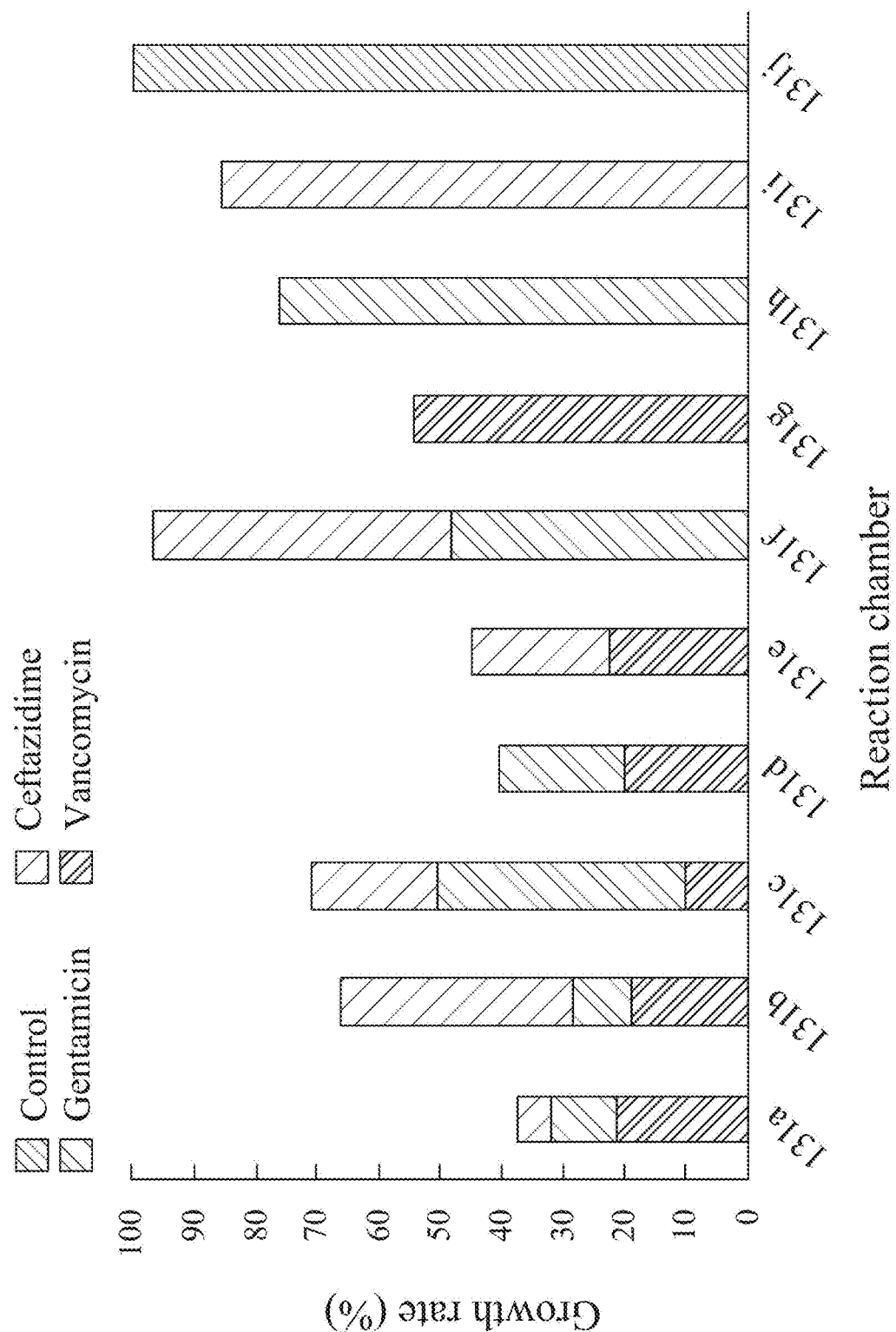
FIG. 11B is an analysis results of the antibiotic susceptibility testing in Example 10.

Please refer to FIG. 11A, FIG. 11B and Table 3. FIG. 11A is colorimetric results of an antibiotic susceptibility testing in Example 10, FIG. 11B is an analysis result of the antibiotic susceptibility testing in Example 10, and results of determining minimum inhibitory concentrations of personalized antibiotic combinations in Example 10 and Comparative Example 2 are listed in Table 3.

TABLE 3

| Antibiotics Combination | Example 10 | Comparative Example 2 |
|---|---|---|
| vancomycin + gentamicin | Synergy | Synergy |
| vancomycin + ceftazidime | Synergy | Synergy |
| Gentamicin + ceftazidime | Antagonism | Antagonism |
| vancomycin + gentamicin + ceftazidime | Synergy | Synergy |

As shown in FIG. 11A, FIG. 11B and Table 3, the determination of the minimum inhibitory concentrations of vancomycin, gentamicin and ceftazidime for the vancomycin-intermediate *Staphylococcus aureus*, which is performed by the automatic microfluidic system for rapid personalized drug screening provided in the present disclosure, obtains the same result with the determination of the minimum inhibitory concentration performed by Comparative Example 2. That is, the automatic microfluidic system for rapid personalized drug screening can automatically perform the antibiotic susceptibility testing of antibiotic combination for the bacteria at the same time, and the determination results can be visually observed. Thus, the cost and time of the antibiotic susceptibility testing can be reduced so as to present a potential for clinical use.

To sum up, the automatic microfluidic system for rapid personalized drug screening can automatically perform the operations such as manual liquid distribution and antibiotic concentration dilution in the traditional antibiotic susceptibility test for single antibiotic or antibiotic combinations through two mixing pumps of a fluid driving unit. The transportation and mixing of fluids can be preciously and efficiently proceeded by the integration of pneumatic micro-pumps and pneumatic micro-valves, and the sample cross-contamination resulted from the conventional operation can be further avoided. Furthermore, compared to the conventional testing method, the automatic microfluidic system for rapid personalized drug screening and testing method for personalized antibiotic susceptibility provided in the present disclosure makes the entire detection process faster, requires less reagent volume, bypasses the manual determination and the usage of expensive equipment, and still can obtain the accurate results. Thus, the automatic microfluidic system for rapid personalized drug screening and testing method for personalized antibiotic susceptibility provided in the present disclosure can screen fast and reduce the labor cost of hospital so as to present an excellent potential on clinical use.

Although the present disclosure has been described in considerable detail with reference to certain embodiments thereof, other embodiments are possible. Therefore, the spirit and scope of the appended claims should not be limited to the description of the embodiments contained herein. In view of the foregoing, it is intended that the present disclosure cover modifications and variations of this disclosure provided they fall within the scope of the following claims.

The invention claimed is:

1. An automatic microfluidic system for rapid personalized drug screening, comprising:
  a microfluidic chip, comprising:
    a fluid storage unit comprising a plurality of fluid storage chambers for storing, respectively, a bacterial suspension, a culture medium and a first antibiotic solution;
    a fluid driving unit communicated and disposed adjacent to the fluid storage unit, wherein the fluid driving unit comprises two mixing pumps in which each of the mixing pumps comprises:
      two pneumatic micro-pumps arranged side by side;
      a mixing chamber stacked at one side of the two pneumatic micro-pumps, and both of the two pneumatic micro-pumps are connected with the mixing chamber; and
      a blocking structure disposed in the mixing chamber and connected between the two pneumatic micro-pumps, wherein the blocking structure is deflected along with an operation of the two pneumatic micro-pumps when the two pneumatic micro-pumps are alternately started;
    a reaction unit communicated with the fluid driving unit and comprising a plurality of reaction chambers radially distributed around the fluid driving unit, wherein each of the reaction chambers is for storing a reaction solution; and
    a plurality of valve units, comprising:
      a plurality of pneumatic micro-valves disposed between the fluid storage unit and the fluid driving unit, and between the fluid driving unit and the reaction unit; and
      a plurality of valve control air holes for controlling opening and closing of the pneumatic micro-valves;
    wherein the microfluidic chip has a chip surface and comprises, in order from the chip surface to a bottom of the microfluidic chip, a first flexible base plate, a second flexible base plate and a bottom plate, the first flexible base plate, the second flexible base plate and the bottom plate are stacked in sequence so as to form the fluid storage unit, the fluid driving unit, the reaction unit and the valve units, and the blocking structure is integrally connected with the second flexible base plate;
    wherein the fluid driving unit is applied for mixing and quantitatively transporting the bacterial suspension, the culture medium and the first antibiotic solution to each of the reaction chambers so as to form the reaction solution.

2. The automatic microfluidic system for rapid personalized drug screening of claim 1, wherein an air channel layer is formed by stacking the first flexible base plate and the second flexible base plate in sequence, a liquid channel layer is formed by stacking the second flexible base plate and the bottom plate in sequence, and the mixing chamber is disposed in the liquid channel layer.

3. The automatic microfluidic system for rapid personalized drug screening of claim 1, wherein the first flexible base plate and the second flexible base plate are made of poly (dimethylsiloxane), and the bottom plate is made of glass.

4. The automatic microfluidic system for rapid personalized drug screening of claim 1, further comprising:
a second antibiotic solution and a third antibiotic solution, wherein each of the second antibiotic solution and the third antibiotic solution is stored, separately, in one of the fluid storage chambers.

5. The automatic microfluidic system for rapid personalized drug screening of claim 1, wherein each of the pneumatic micro-valves is a normally-closed micro-valve.

6. The automatic microfluidic system for rapid personalized drug screening of claim 1, wherein two of the fluid storage chambers are disposed between the two mixing pumps.

7. The automatic microfluidic system for rapid personalized drug screening of claim 1, further comprising:
a temperature control apparatus stacked with the microfluidic chip for controlling a temperature of the microfluidic chip within a predetermined range.

8. The automatic microfluidic system for rapid personalized drug screening of claim 1, wherein the culture medium comprises an oxidation-reduction indicator.

9. The automatic microfluidic system for rapid personalized drug screening of claim 8, wherein the oxidation-reduction indicator is resazurin.

10. The automatic microfluidic system for rapid personalized drug screening of claim 8, further comprising:
an absorbance detection device for detecting an absorbance or a fluorescent value of the reaction solution after an incubation time.

* * * * *